United States Patent
Sujdak

(10) Patent No.: US 6,847,836 B1
(45) Date of Patent: Jan. 25, 2005

(54) EMERGENCY ECG ELECTRODE CHEST PAD

(76) Inventor: Lenny Sujdak, 6738 Greenleaf St., Woodridge, IL (US) 60517

(*) Notice: Subject to any disclaimer, the term of this patent is extended or adjusted under 35 U.S.C. 154(b) by 388 days.

(21) Appl. No.: 10/071,681

(22) Filed: Feb. 8, 2002

(51) Int. Cl.$^7$ ............................................. A61B 5/0408
(52) U.S. Cl. ...................... 600/382; 600/386; 600/391; 600/392; 600/393
(58) Field of Search ................................ 600/382, 386, 600/391–393

(56) References Cited

U.S. PATENT DOCUMENTS

| | | | |
|---|---|---|---|
| 4,121,575 A | 10/1978 | Mills et al. | 128/2.06 E |
| 4,233,987 A | 11/1980 | Feingold | 128/639 |
| 4,608,987 A | 9/1986 | Mills | 128/639 |
| 4,957,109 A | 9/1990 | Groeger et al. | 128/640 |
| 5,007,427 A | 4/1991 | Suzuki et al. | 128/659 |
| 5,042,481 A | 8/1991 | Suzuki et al. | 128/639 |
| 5,184,620 A | 2/1993 | Cudahy et al. | 128/639 |
| 5,224,479 A | 7/1993 | Sekine | 128/644 |
| 5,327,888 A | 7/1994 | Imran | 128/640 |
| 5,868,671 A | 2/1999 | Mahoney | 600/382 |
| 5,938,597 A | 8/1999 | Stratbucker | 600/382 |
| 6,157,851 A | 12/2000 | Kelly et al. | 600/386 |
| 6,173,198 B1 | 1/2001 | Schulze et al. | 600/382 |
| 6,532,379 B2 * | 3/2003 | Stratbucker | 600/382 |
| 6,560,473 B2 * | 5/2003 | Dominguez | 600/382 |

* cited by examiner

Primary Examiner—Lee S. Cohen
(74) Attorney, Agent, or Firm—Piper Rudnick LLP

(57) ABSTRACT

An ECG electrode chest pad particularly adapted for use in emergency room situations having upper fit portions with upper limb electrodes, and elongated central or medial base fit portion with a plurality of precordal unipolar electrodes and lower fit portions with lower limb electrodes, said electrodes being attached to leads which are internal to the base chest pad and terminate into at least one lead branch adapted to plug into an ECG monitor and having a perforation in the base pad material such that one group of electrodes may be separated from a second group of electrodes to facilitate ease of patient monitoring and complimentary medical procedures.

12 Claims, 4 Drawing Sheets

EMERGENCY ECG ELECTRODE CHEST PAD

BACKGROUND OF THE INVENTION

1. Field of Invention

This invention relates to a electrocardiogram (ECG) diagnostic device, and more specifically, to a disposable ECG diagnostic chest pad having pre-positioned lead electrodes and internal wiring which may be placed quickly as a single unit upon a patient and may be separated into two sections by way of perforated sections in the underling pad material, thus allowing greater flexibility in monitoring and diagnosing a patient's electrocardiogram waves.

2. Description of Prior Art

It has been long known in the medical community that the current condition, and possibly future state, of a subject patient's heart muscle can be ascertained by measuring the cardiac electrical activity. The electrical system of the heart not only initiates and controls the rate of heartbeat, but also coordinate to transmission in the most efficient mechanical manner. When such electric signals are irregular, it is a sign of cardiac problems, particularly cardiac arrest, better known as a "heart attack."

Like all electrical signals, the electrical signals generated by the heart can be expressed as a wave or a series of waves having a frequency and amplitude. Again, like all electrical signals, these waves can be detected and measured—in this case by an electrocardiograph. Electrodes, generally pads containing conductive material, such as silver chloride and an adhesive are attached to the trunk and limbs of a patient's body. The electrodes are in turn attached to "leads" or cables which are connected to the electrocardiograph. Generally, in modem medical practice a ten-lead electrocardiograph is used to produce twelve lead measurements through the use of bipolar electrodes. The electrocardiograph receives the signals from the leads, processes them and outputs the resulting waveform patterns, usually on a strip of moving paper. These resulting patterns are known as an electrocardiogram (ECG). By viewing the resulting ECG output, the physician or other healthcare professional can determine the current condition of the patient's heart muscle and can compare such pattern against healthy and known abnormal patterns. As such, an initial diagnosis of the patient's condition can be made.

The majority of electrocardiological testing is performed in hospital emergency rooms where time of patient treatment of the essence in order to obtain a positive outcome. Trained personnel are required to properly position the electrodes onto the chest wall and limbs of the patient and connect the corresponding wires. In an emergency room situation, this procedure must be performed with speed and accuracy. The work of attaching the ten or twelve electrodes and the corresponding leads can be time consuming. In addition, the leads tend to clutter up the chest area, making additional emergency medical procedures more difficult to perform. Such problems associated with this process are increased when the patient is a small child or an infant.

Traditional prior art electrocardiograph systems typically utilize electrodes comprising elastic cloth or other material having moderate flexibility together with rigidity and strength, such as rubber, synthetic rubber or porous synthetic resins having air permeability. Lead cables are attached either externally or internally and are connected to a control box mounted on the pad. The pad is fastened with belt- or strap-like means, which must wrap around the subject's waist, chest, and arms. These pads are generally used for long term monitoring, and are not typically disposable. For the short-term use in the emergency room, single disposable electrodes are individually applied, with an adhesive backing, to the patient's body at the designated optimal locations. The corresponding leads from the electrocardiograph are then attached to the electrodes by any number of means known in the art, such as alligator clips or plugs. As previously mentioned this process is cumbersome and time consuming, particularly within an emergency situation. Under such circumstances, the electrodes may be incorrectly placed or fall off the patient, thus requiring additional time for replacement upon the patient.

Several solutions are presented in the prior art which attempt to solve some of the aforementioned problems by pre-positioning the leads. The first general solution seen in the art is a vest that contains the leads built into the material. Two such examples are an "Apparatus for Transmitting ECG Data," to Mills, U.S. Pat. No. 4,608,987 and an "ECG Diagnostic Pad," to Sekine, U.S. Pat. No. 5,224,479. By having the leads prepositioned within the vest, the entire apparatus can be placed upon the patient and immediately used, thus saving valuable time. However, such vests, including those seen in Mills and Sekine, have several drawbacks. First, these vests must be made in multiple sizes in order to fit the vast multitude of patient sizes and shapes from infant to adult and from thin to overweight. Production and acquisition costs are increased as well as the storage space needed to stock a supply of multiple, different-sized vests. The amount of materials used for an entire vest also adds to cost concerns. Most prior art vests are not disposable and reuse and refurbishment costs may be prohibitive.

A second solution presented in the prior art is the use of "electrode strips." In these devices, the electrodes placed within a strip of material, usually containing an adhesive backing layer. The leads are generally wired into the strip. When need, the adhesive backing is exposed or adhesive otherwise applied and the strip is positioned and affixed to the patient's torso. Representative examples can be see in U.S. Pat. No. 4,233,987 to Feingold, U.S. Pat. No. 5,184,620 to Cudahy et al. and U.S. Pat. No. 5,868,671 to Mahoney. While cheaper to produce, store and use than vests, these and other prior art strips do have their drawbacks. First, may of the prior art electrode strips, such as the device illustrated and claimed in the Cudahy et al. patent, utilize leads which are positioned only across the torso of the patient. Readings from the upper and lower extremities cannot be taken or optimal positioning cannot be obtained. The Feingold strip allows individual placement, but having only three leads, it is likely that the medical professional would not utilize placement at the extremities. Another drawback to prior art electrode strips is their inability to be used to monitor a patent. Often, after the initial diagnosis, a physician or other medical professional may wish merely to monitor the patient's cardiac activity. As such, only certain leads of the ECG need to be used. It is, again, preferable, to eliminate as leads and other materials from the patient's chest in order to allow room for other procedures. Using the conventional technique of placement of individual leads, the unnecessary leads can be removed. However, in prior art electrode strips, one cannot remove the unnecessary electrodes without also removing the electrodes needed for the monitoring function.

It is therefore an object of the present invention to provide a means for quickly and accurately positioning electrodes and leads for electrocardiographic analysis.

It is a further object of the present invention to provide an electrocardiographic electrode pad that provides signals from the torso and extremities of a patient.

It is yet another object of the present invention to provide an electrocardiographic electrode pad that can be used for patient monitoring.

It is an additional object of the present invention is to provide inexpensive and disposable ECG diagnostic pad which can be attached and removed quickly so as to not interfere with other procedures such as chest X-rays.

SUMMARY OF INVENTION

To attain the objects described above according to this invention, there is provided an ECG diagnostic pad comprising a pad base with upper fit portions with upper limb lead electrodes, a central fit portion with unipolar precordial lead electrodes and a lower portion with flank lead electrodes. The corresponding electrode wires, connecting the pad to the monitoring unit, are embedded in the pad internally to eliminate clutter and time of attaching them to the electrodes. The pad is attached with an adhesive, which is on the backside of the pad eliminating the need for belts or straps. By attaching the pad to the chest wall of a human subject or patient, all of the pre-wired electrode leads come in contact with the proper locations simultaneously, allowing rapid connection to the ECG monitor in a one-step process.

In the most preferred embodiment, the inventive ECG electrode pad contains a perforation between leads V1 and V2 which would allow the easy removal of leads V2–V6, when monitoring is required without the need for a full twelve lead ECG. Leads V2–V6 can be easily applied separately if the patent requires a full twelve lead ECG later.

This and other features, aspects and advantages of the present invention will appear and become better understood from the following description in which the preferred embodiments are set forth in detail in conjunction with the appended claims and accompanying drawings.

BRIEF DESCRIPTION OF THE DRAWINGS

Specific embodiments of the invention have been chosen for purposes of illustration and description, and are shown in the accompanying drawing, forming a part of the specification wherein.

DESCRIPTION OF PREFERRED EMBODIMENTS

Figure 1:
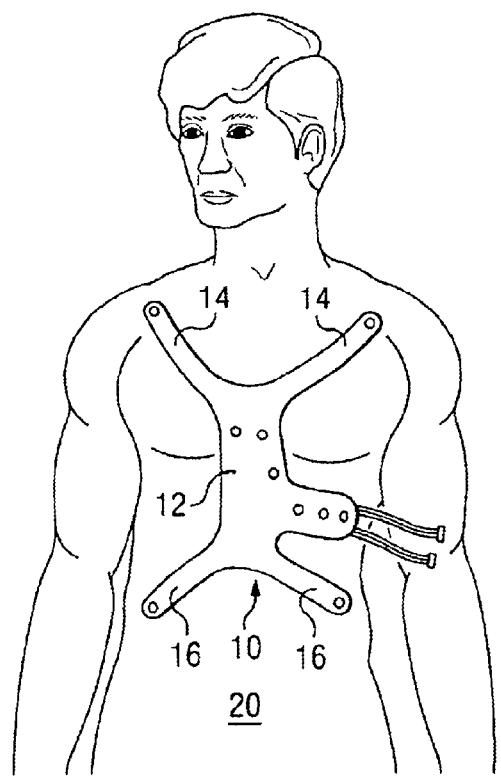
FIG. 1 is a perspective view of a human subject fitted with one embodiment of the emergency ECG electrode pad according to the present invention.

Referring to FIG. 1, the preferred embodiment of the ECG electrode chest pad 10 according to this invention is shown. The base ECG electrode chest pad 10 is generally comprised of a medial portion 12, upper fit portions 14 and lower fit portions 16 such that the entire pad forms the general shape of an elongated "X" with an additional line extending from the center to the right, to reduce the surface area of the invention. As is shown in FIG. 1, the pad 10 is placed upon the patient 20 such the upper fit portions 14 extend aslant upward and are generally at the patient's shoulders and that the medial portion 12 extends generally down the patient's sternum and to the left across the chest wall, below the heart. The lower fit portions 16 extend aslant downward and should therefore be around the lower abdomen of the patient 20. In order to accommodate patients of various sizes, it is contemplated that invention would be manufactured in at least five different sizes: infant, small, medium, large, and extra large.

The chest pad 10 is preferably made of a flexible, breathable or porous material known in the art, such as cotton, polyester or, most preferably, foam. The material, preferably is also radiologically transparent to x-rays and other diagnostic procedures, such as ultrasound and magnetic resonance imaging (MRI). An adhesive is applied reverse side of the pad 10. (shown in FIG. 3). Any temporary medical adhesive known in the art may be used with the instant invention so long as it does not distract from the function of the pad 10 or patient comfort. The adhesive preferably is applied to the entire back surface of the pad 10 and covered with a backing (not shown) until needed. In the alternative, the adhesive can be applied to several contact points across the back of the pad 10 during manufacture and covered with a backing until use or, less preferably, the adhesive is applied just prior to use.

Figure 2:
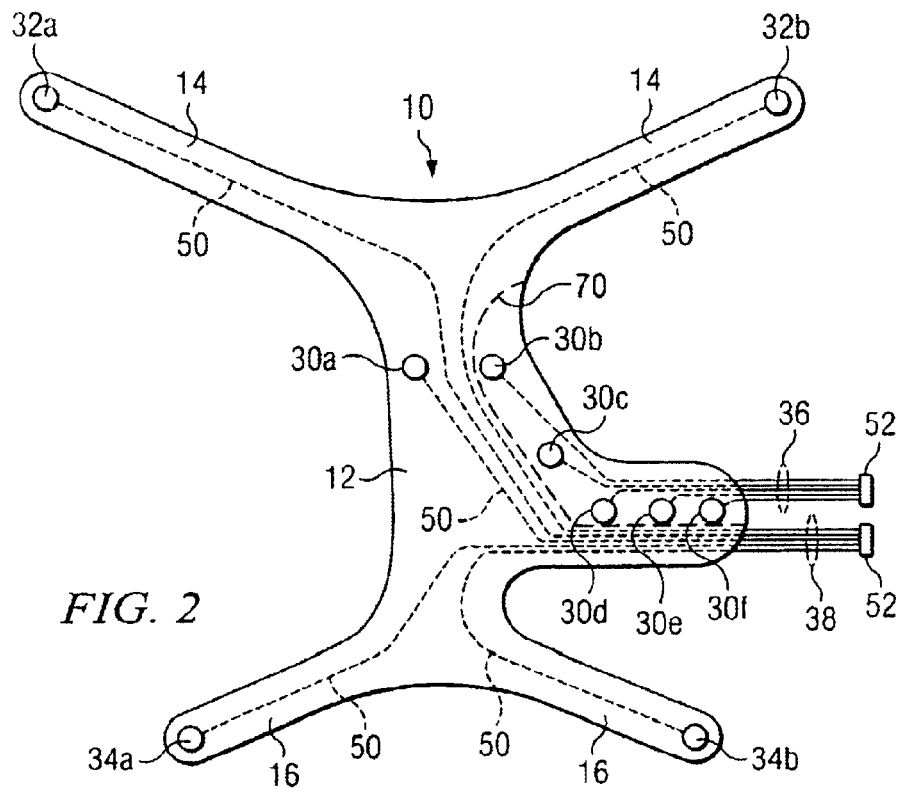
FIG. 2 is a top of the pad in FIG. 1.
Figure 3:
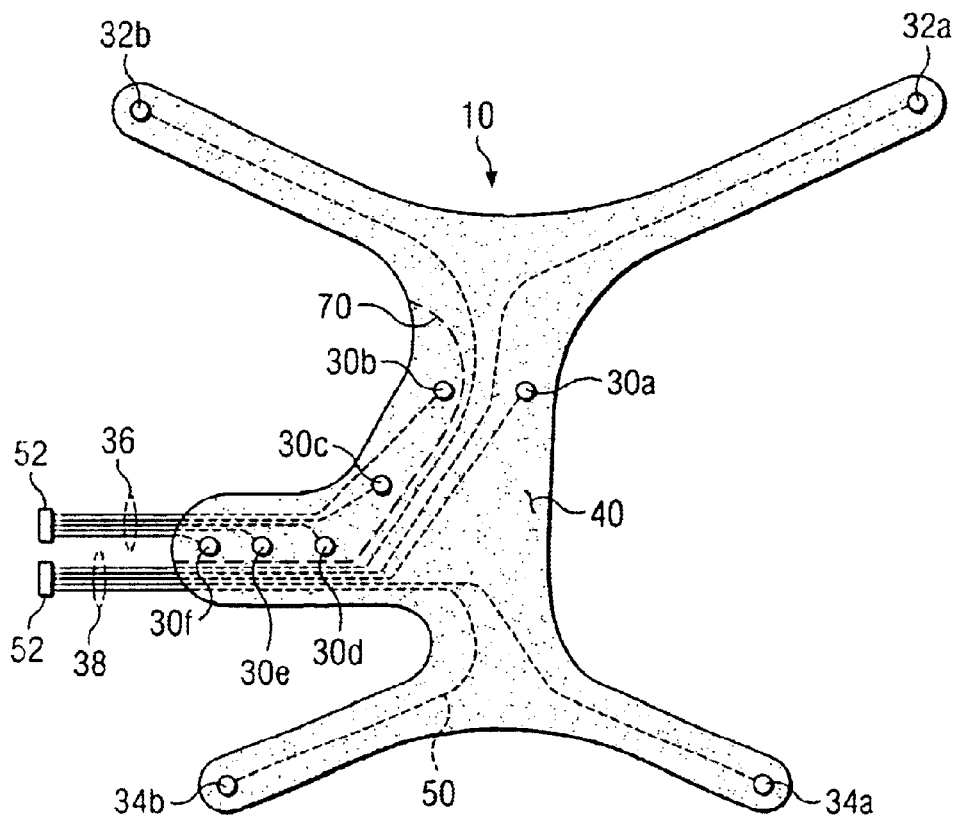
FIG. 3 is a bottom view (patient contact side) of the pad in FIG. 1.

A more detailed close-up of the ECG electrode pad 10 is shown in FIG. 2. As can be seen, the pad 10 contains a series of electrodes 30–34 that are in turn electrically connected to two wiring harnesses 36 and 38. The medial portion 12 contains six unipolar precordial lead electrodes 30a (V1), 30b (V2), 30c (V3), 30d (V4), 30e (V5) and 30f (V6) which contact the patient 20 from the midriff to the flank. The upper fit portions 14 contain a right-limb electrode 32a and a left-limb electrode 32b for detecting bipolar and unipolar ECG currents. Accordingly, the lower fit portions 16 contain a right-flank electrode 34a and a left-flank electrode 34b that detect bipolar and unipolar ECG currents. The reverse side of FIG. 2 is shown in FIG. 3. In this view, an adhesive 40 is applied to the entire surface of the pad 10, per one embodiment of this invention. When the pad 10 is applied to the patient 20 chest all three portions, 10, 12, and 14 and their respective electrodes 30–34 simultaneously come in contact with the patient.

Each of the electrodes are electrically attached to leads or wires 50. These leads 50 are placed within the material of the ECG pad 10 and are thus integral thereto. The leads 50, in turn, terminate and form two lead bundles 36 and 38. The leads 50 of electrodes 32a–b, 34a–b and 30a form the lower lead bundle 38 while the upper bundle 36 is formed from the leads 50 of electrodes 30b–f. Both bundles 36 and 38 terminate with plugs 52 that are adapted to quickly and easily plug into an ECG monitor 60 to relay signals from the electrodes. Because the electrodes are pre-wired, by coupling the plugs 36 and 38 with the ECG monitor 60, the patient would ready for an electrocardiograph diagnosis without having to make repetitive connections for each lead 50. In addition, the clutter of external wires is eliminated. As shown particularly in FIGS. 1–3 both bundles are located in the center or medial portion 12 of pad 10. It is also contemplated that for better ease of use and separation of the pad 10 into two portions as detailed herein, bundle 38, and the wires 50 associated therewith, would terminate in the lower fit portion 16, towards lead 34b.

Figure 4:
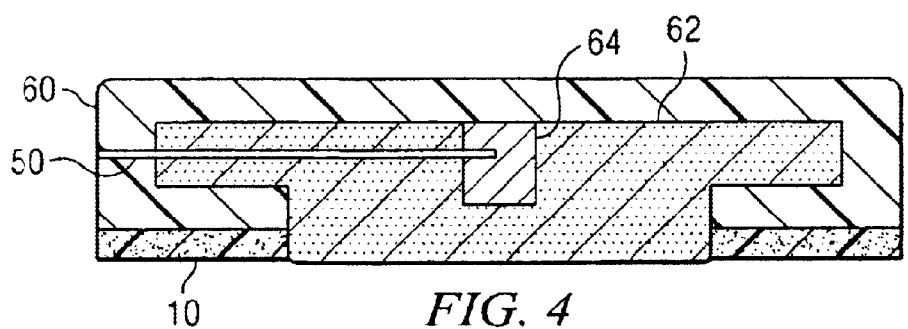
FIG. 4 is a sectional view of a representative lead electrode used in one embodiment of the present invention.

FIG. 4 illustrates a cross-section of an typical electrode in the subject invention Each lead electrodes, such as electrode 30a, is comprised of a casing 60, containing Ag/AgCl solid conductor gel 62, which is mounted in the pad 10. The Ag/AgCl solid conductor gel 62 is exposed on the backside of the pad 10 to ensure contact with the chest wall. Embedded in the center of the Ag/AgCl solid conductor gel 62 is a solid metal stud 64. Stud 64 can be made of any conductive metal or alloy known in the art. It is contemplated that inventive ECG pad can also utilize other types of electrodes now used in the art or later discovered, that may or may not use metal studs and/or conductive gel, so long as an appropriate signal is delivered from the patient to the ECG monitor 60.

Referring again to FIGS. 2 and 3, an important feature of the most preferred embodiment of the subject invention is illustrated. The material of pad 10 contains a perforation 70 which runs from the upper fit portion 14 containing electrode 32b (left-flank), between electrodes 30a (V1) and 30b (V2) and underneath electrodes 30c–30f (V3–6). This feature allows removal before or during application of the ECG pad 10 of leads 30b–30f (V2–V6). In certain circumstances, the physician or other health care profession may merely wish to monitor the patient without the need for a full twelve lead ECG. In general, electrodes 30b–30f and attached leads 50 are not needed for monitoring. In addition, the space otherwise taken up on the patient's chest with these leads may be needed for another medical procedure or instrument. The use of perforation 70 allows an easy one-step removal of these leads. Leads 30b–30f (V2–V6) can be easily applied separately if the patent requires a full twelve lead ECG later.

Figure 5:
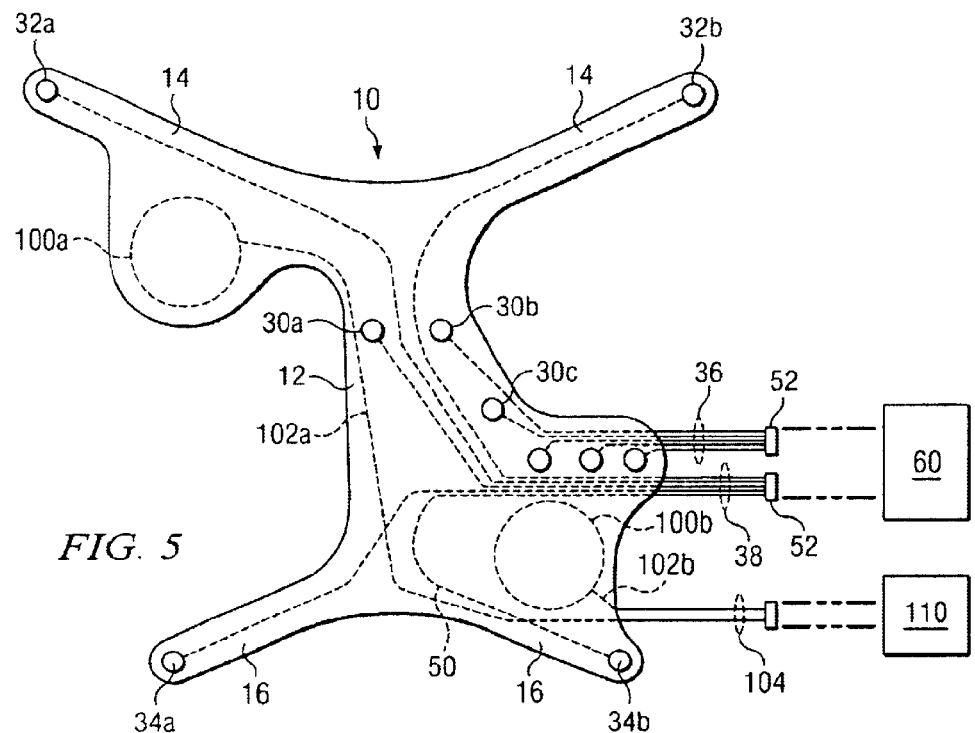
FIG. 5 is a top view of another embodiment of the subject invention with external pacer pads.
Figure 6:
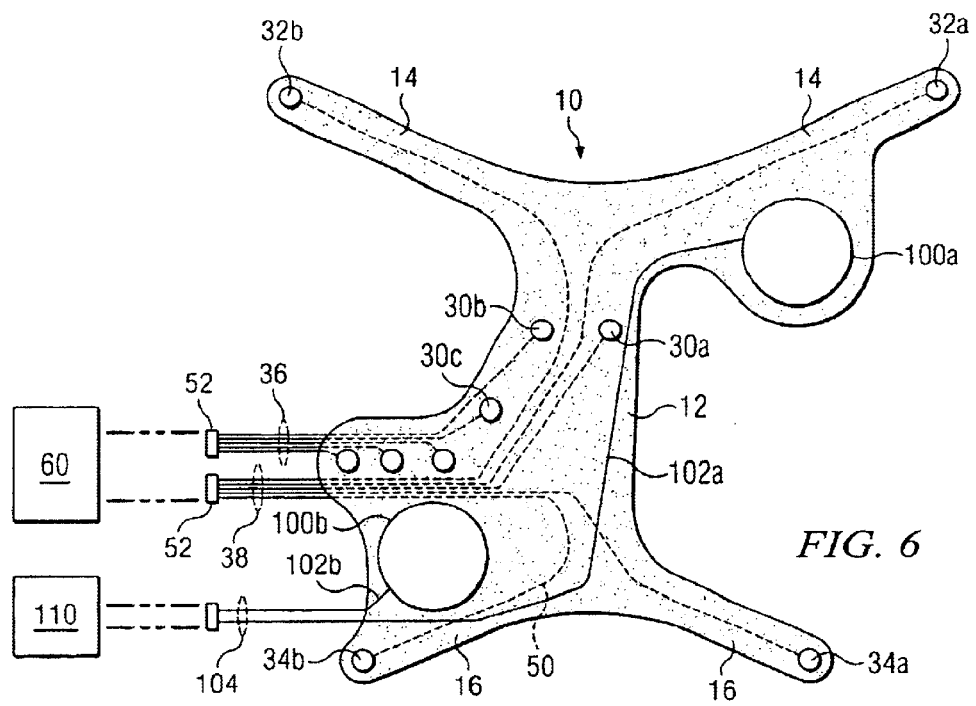
FIG. 6 is a bottom view (patient contact side) of the pad in FIG. 5.

FIGS. 5 and 6 illustrate a second embodiment of the subject invention. In addition to the structures and features detailed in the preferred embodiment, it is contemplated that external pacer pads 100a and 100b can be added to the device. The external pacer pad 100a is located just below the right upper fit portion 14 of the pad 10 and external pacer pad 100b is located just below the horizontal central fit portion 12, which are the proper positions for the prescribed anatomical locations. Like an implanted pacemaker, pacer pads 100 and 100 serve to provide an electrical pulse to the heart to correct an irregular heartbeat. Pacer pads 100a and 100b are electrically connected to pacer control instrument 110 by way of wires 102a and 102b that form a pacer plug bundle 104. Although wires 102a and 102b can be embedded in the fabric of pad 10, the are preferably left free or retained to the exterior of the pad 10 by the minimal use of an adhesive such that the wires 102a–b can easily be moved or removed with the pacer pads 100a–b, as further described herein. Like the electrode plug bundles 36 and 38, the pacer plug bundle 104 can quickly be attached and detracted to the pacer control instrument 110. The control instrument 110, alone or in conjunction with the ECG monitor 60, can measure and monitor the patient's heartbeat and if irregular can administer a corrective electric pulse to the patient by way of the pacer pads 100a and 100b. A perforation 70 can also be incorporated into this embodiment such that electrodes 30b–30f (V2–V6) can be removed, as previously described in the primary embodiment of the inventive ECG pad. Conversely, the portion of the medial pad portion 12 containing electrodes 30a, 32a, 32b, 34a, and 34b and the pacer pads 100a and 100b can be retained on the patient, thus allowing continued pacing. One additional variation of this embodiment results from the use of additional perforations in the pad 10 in lieu of or in addition to perforation 70 which allow separation of all of the electrodes 30a–f, 32a–b, and 34a–b, thus removing the pacer pads 100a and 100b and wires 102a and 102b from the patient and leaving electrodes 30a–f, 32a–b and 34a–b attached to the patient. In the alternative, pacer pads 100a and 100b and wires 102a and 102b can be left on the patient and electrodes 30a–f, 32a–b and 34a–b removed.

Figure 7:
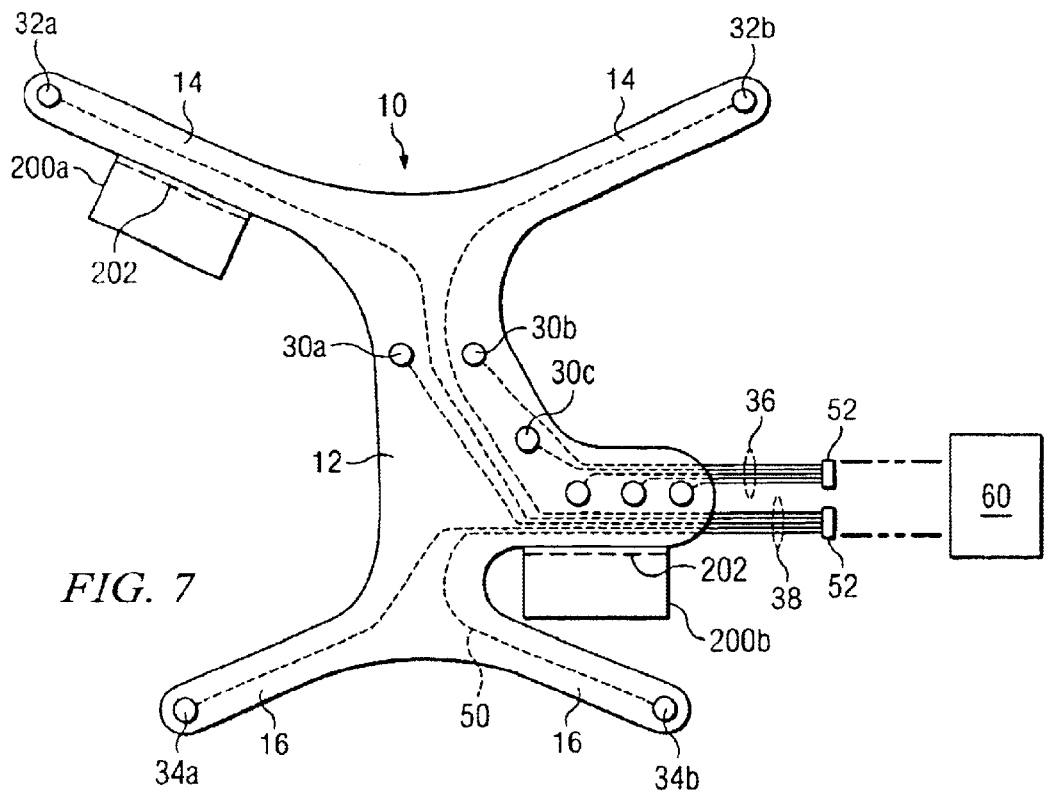
FIG. 7 is a top view of another embodiment of the subject invention with defibrillation pads.
Figure 8:
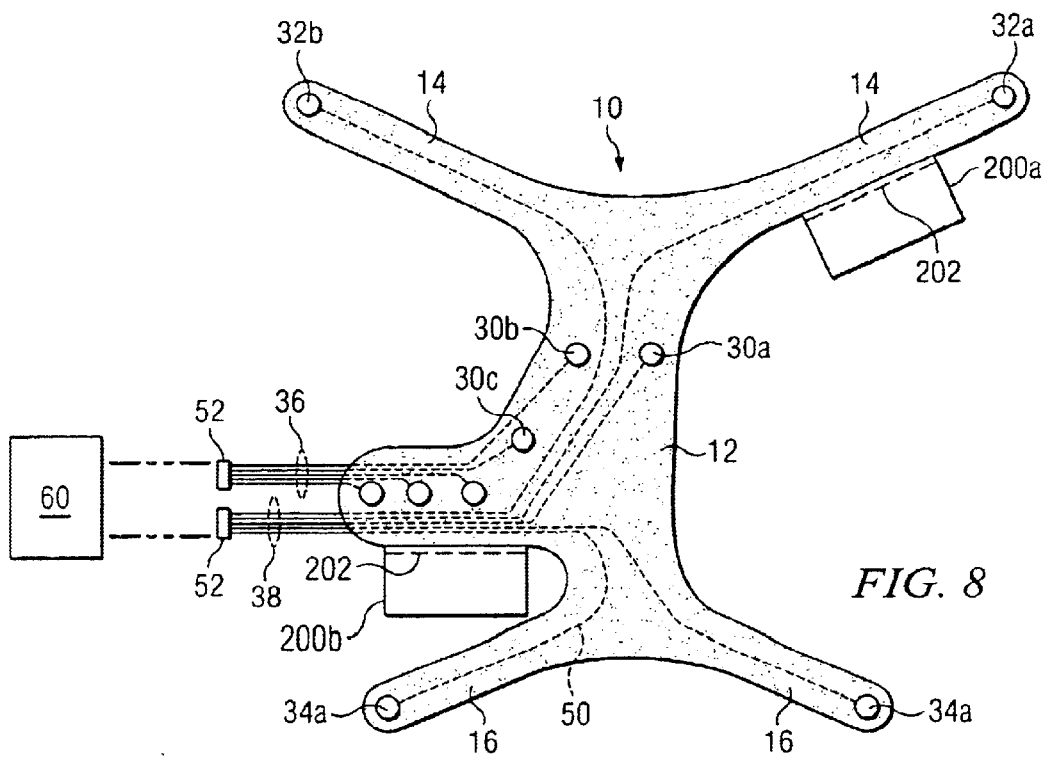
FIG. 8 is a bottom view (patient contact side) of the pad in FIG. 7.

A third embodiment of the invention is illustrated with reference to FIGS. 7 and 8. In addition to the structures and features detailed in the preferred embodiment, it is contemplated that defibrillator pads 200a and 200b properly positioned for the prescribed anatomical locations can be added to the ECG electrode pad 10. The defibrillator pad 200a is located just below the right upper fit portion 14 of the pad 10 and defibrillator pad 200b is located just below the horizontal central fit 12 portion of the pad 10. The defibrillator pads 200a and 200b are made of a flexible solid conductor gel to ensure contact with the patent and can be adhered to the patient as know in the art, consistent with the techniques used for the main ECG pad 10. If defibrillation of the patient is required, the physician can applied the defibrillation paddles of the defibrillator directly to pads 200a and 200b without use of separate conductor gel. As previously described in the primary embodiment of the inventive ECG pad, a perforation 70 can also be incorporated into this embodiment such that electrodes 30b–30f (V2–V6) can be removed. Conversely, the portion of the medial pad portion 12 containing electrodes 30a, 32a, 32b, 34a, and 34b and the defibrillator pads 200a and 200b can be retained on the patent, thus allowing continued defibrillation of the patient. Perforations 202 can also be formed between the defibrillator pads 200a and 200b and the medial pad portion 12, to allow removal of the defibrillator pads 200a and 200b from medial pad 12.

In addition to the uses immediately described above, it will be apparent to those skilled in the art that other modifications and variations can be made the method of the instant invention without diverging from the scope, spirit, or teaching of the invention. Therefore, it is the intention of the inventors that the description of instant invention should be considered illustrative and the invention is to be limited only as specified in the claims and equivalents thereto.

What is claimed is:

1. An electrocardiogram diagnostic chest pad comprising:
   a base pad comprised of a lightweight material and having a central body portion, a central fit portion extending from the central body portion, a plurality of upper fit portions, and a plurality of lower fit portions;
   a first set of a plurality of electrodes attached to said base pad, each of said first set of plurality of electrodes being connected to a lead capable of conducting electric signals and each said lead embedded with the base pad material and terminating at a first lead bundle having a plug adapted input to an ECG monitor;
   a second set of a plurality of electrodes attached to said base pad, each of said second set of plurality of electrodes being connected to a lead capable of conducting electric signals and each said lead passing through the base pad material and terminating at a second lead bundle having a plug adapted input to an ECG monitor; and
   a perforation in the material of the base pad between the first set of plurality of electrodes and the second set of plurality of electrodes,
   whereby the chest pad can be used as a whole or separated into two distinct sections for varying ECG measurement and monitoring functions.

2. The electrocardiogram diagnostic chest pad of claim 1 further comprising a first and second upper fit portion and a first and second lower fit portion.

3. The electrocardiogram diagnostic chest pad of claim 2 wherein said first set of plurality of electrodes comprises a first electrode on said first upper fit portion, a second electrode on said second upper fit portion, a third electrode on said central body portion, a fourth electrode on said first lower fit portion and a fifth electrode on said second lower fit portion.

4. The electrocardiogram diagnostic chest pad of claim 2 wherein said second set of plurality of electrodes comprises first and second electrodes on said central body portion, and third, fourth and fifth electrodes on said central fit portion.

5. The electrocardiogram diagnostic chest pad of claim 1 wherein each of the first and second sets of electrodes further comprise a solid metal stud embedded within a silver/silver chloride conductor gel.

6. The electrocardiogram diagnostic chest pad of claim 1 further comprising a plurality of pacer pads, each of said plurality of pacer pads being connected to a lead embedded within the material of the base pad and terminating in a plug bundle adapted for connection to a pacer control instrument.

7. The electrocardiogram diagnostic chest pad of claim 1 wherein the base pad further comprises an external side and a patient contact side and said patient contact side further comprises a plurality of adhesive portions, each containing a removable backing, whereby a health care professional can remove the removable backing, expose each adhesive portion and adhere the chest pad to a patient.

8. The electrocardiogram diagnostic chest pad of claim 2 wherein the base pad is radiologically transparent to x-rays.

9. The electrocardiogram diagnostic chest pad of claim 1 further comprising a plurality of defibrillator pads.

10. The electrocardiogram diagnostic chest pad of claim 9 further comprising a perforation between the base pad and each of the plurality of defibrillator pads.

11. The electrocardiogram diagnostic chest pad of claim 9 wherein each of the plurality of defibrillator pads further comprises a flexible solid conductor gel.

12. An electrocardiogram diagnostic chest pad comprising:
  a base pad comprised of a lightweight, breathable material and having a central body portion, a central fit portion extending from the central body portion, first and a second upper fit portions extending aslant upwards from said central body portion and away from each other and first and second lower fit portions extending aslant downwards from said central body portion and away from each other;
  a first set of electrodes attached to said base pad, comprising a first electrode on said first upper fit portion, a second electrode on said second upper fit portion, a third electrode on said central body portion, a fourth electrode on said first lower fit portion and a fifth electrode on said second lower fit portion, each of said first set of electrodes being connected to a lead capable of conducting electric signals and each said lead embedded with the base pad material and terminating at a first lead bundle having a plug adapted input to an ECG monitor;
  a second set of electrodes attached to said base pad comprising first and second electrodes on said central body portion, and third, fourth and fifth electrodes on said central fit portion, each of said second set of electrodes being connected to a lead capable of conducting electric signals and each said lead passing through the base pad material and terminating at a second lead bundle having a plug adapted input to an ECG monitor; and
  a perforation in the material of the base pad between the first set of electrodes and the second set of electrodes, whereby the chest pad can be used as a whole or separated into two distinct sections for varying ECG measurement and monitoring functions.

* * * * *